United States Patent [19]

Choi

[11] Patent Number: 4,839,926

[45] Date of Patent: Jun. 20, 1989

[54] CAP WITH BINOCULARS

[75] Inventor: Hae Y. Choi, Seoul, Rep. of Korea

[73] Assignee: Un Shik Shin, Rep. of Korea

[21] Appl. No.: 206,822

[22] Filed: Jun. 15, 1988

[51] Int. Cl.$^4$ .............................................. A42B 1/24
[52] U.S. Cl. ............................................ 2/199; 2/10;
2/12; 351/155
[58] Field of Search ............... 2/12, 199, 10; 350/145;
351/45, 155, 158

[56] References Cited

U.S. PATENT DOCUMENTS

| | | | |
|---|---|---|---|
| 700,587 | 5/1902 | Waldron | 351/155 |
| 1,313,469 | 8/1919 | Crossley | 2/12 |
| 1,789,552 | 1/1931 | Judd | 2/12 |
| 2,406,598 | 8/1946 | Flood | 2/12 |
| 4,449,787 | 5/1984 | Burbo | 350/145 |

Primary Examiner—Werner H. Schroeder
Assistant Examiner—D. Biefeld
Attorney, Agent, or Firm—Banner, Birch, McKie and Beckett

[57] ABSTRACT

A cap with binoculars for using, both as a cap and binoculars, comprising a first member, a second member, pin means and binoculars.

13 Claims, 3 Drawing Sheets

U.S. Patent Jun. 20, 1989 Sheet 1 of 3 4,839,926 ized image must be reconstructed 

CAP WITH BINOCULARS

FIELD OF THE INVENTION

This invention relates to a cap with binoculars suitable for watching sports and the likes, and more particularly, to a double functioning cap with binoculars that can effectively perform both functions of a cap and binoculars.

BACKGROUND OF THE INVENTION

Since binoculars are usually carried by hand, they are very inconvenient to continue to use and carry for many hours.

SUMMARY OF THE INVENTION

It is, therefore, an object of the present invention to provide a cap with binoculars which can perform both the functions of a cap and binoculars.

A further object of the present invention is to provide a cap with light-weight binoculars which can be conveniently used and carried for many hours.

In accomplishing these and other objects, according to the present invention, there is provided a cap with binoculars which includes a first member and a second member thereof. The first member includes in it a binoculars receiving portion formed integrally on the visor, a latch forming portion and pin holes. The second member includes a band, a a supporting protrusion and pin holes. The first member is attached to the second member by means of pin means. The binoculars are mounted within the binoculars receiving portion. The first member can be shifted from the normal position to a down-position by swinging the visor downward. Thus, both the functions of a cap and binoculars are easily accomplished.

BRIEF DESCRIPTION OF THE DRAWINGS

These and other objects and advantages of the present invention are more fully specified in the following description with reference to the drawings in which.

DETAILED DESCRIPTION OF THE PREFERRED EMBODIMENTS

Figure 1:
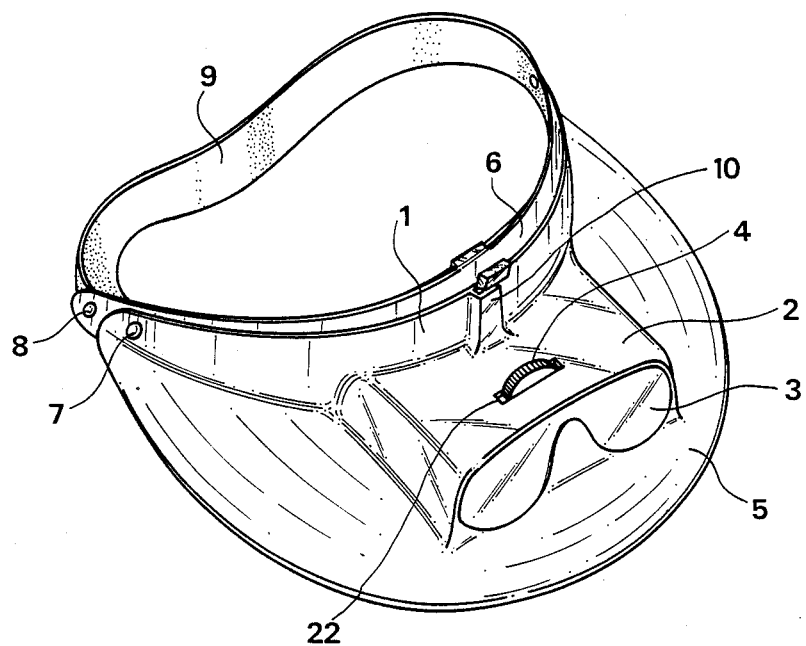
FIG. 1 is a perspective view of an embodiment of the present invention.
Figure 2:
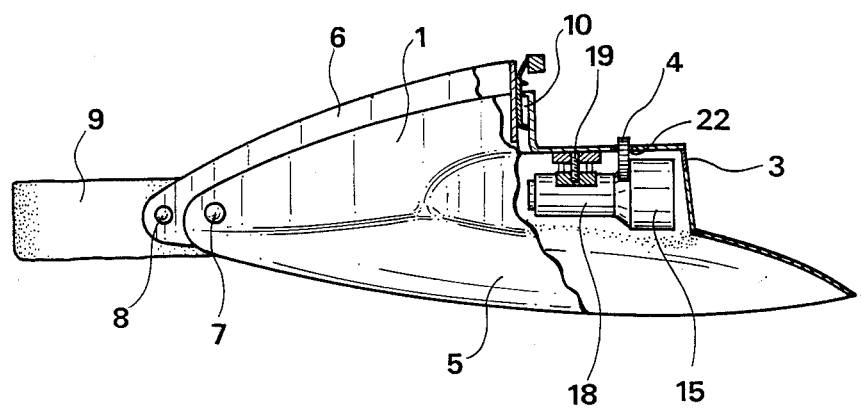
FIG. 2 is a side elevation view, partly in cutaway, of the embodiment.

Referring to FIGS. 1, 2 and 3, a cap according to the invention has a first member(1) and a second member(6) thereof. The first member(1) includes a latch receiving groove(10) formed in the center of the vertical semicircular portion thereof, a visor(5), and a binoculars receiving portion(2) formed integrally on the visor(5). The second member(6) includes a resilient cotton band(9) attached to the second member(6) by means of connecting hooks(8) and suitable hook means formed in the inner surface of the vertical semicircular portion thereof. The first member(1) is attached to the second member(6) by means of connecting pins(7). Thus, the first member(1) can be moved either down or upward with respect to the second member(6).

On the other hand, the binoculars receiving portion(2) is formed integrally on the visor(5), as described above and the upper surface of the portion(2) has an opening(22) for actuating an adjusting knob(4). Also, protecting glass(3) is mounted on the front surface of the portion(2). Though will be described hereinafter, such light-weight binoculars are inserted within the portion(2) and are mounted by means of a suitable holding means such as designated refrence number(19), as shown in FIG. 3. It is to be noted that when binoculars are heavy weighted, they are very inconvenient to use for various purposes.

Figure 5A:
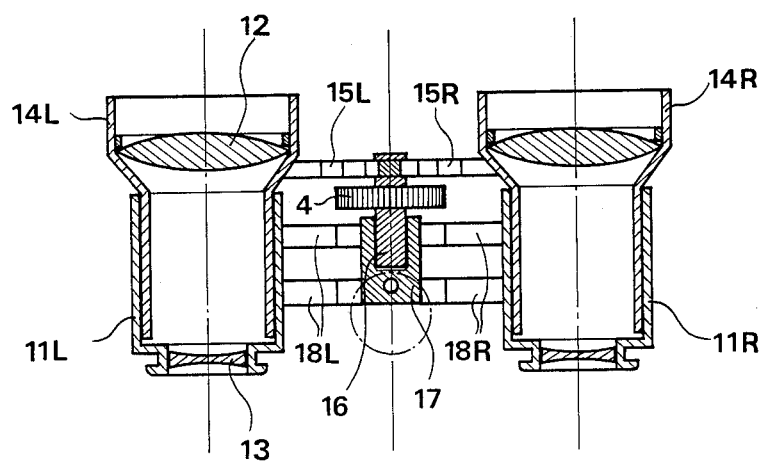
FIG. 5(a) is a detailed sectional view of the binoculars.

FIG. 5 illustrates the light-weight binoculars. Left and right objective lens cases(14L, 14R) can be telescopically inserted into left and right eyepiece cases(11L, 11R), respectively. The eyepiece and objective cases have an eyepiece(13) and an objective lens(12), respectively, and the cases(11L, 11R; 14L, 14R) are made of light-weight materials such as plastics and rubber.

A right front supporting member(15R) and a left front supporting member(15L) which are connected to the objective lens cases (14R, 14L) respectively, are constructed so that the members(15L, 15R) can be folded towards each other about an outer-threaded rod(16). In front of the supporting members(15L, 15R), the adjusting knob(4) connected to the rod(16) is provided. Therefore, the left and right front supporting members(15L, 15R) can be folded about the axis of the rod(16) and the adjusting knob(4).

Figure 5B:
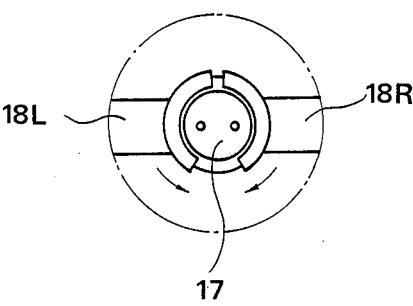
FIG. 5(b) illustrate the operation of the left and right supporting members.

In like manner, between the left and right eyepiece cases, a right rear supporting member(18R) and a left rear supporting member(18L) which are connected to the eyepiece cases(11R, 11L) respectively, are constructed so that the members(18L, 18R) can be folded towards each other about an inner-threaded cylinder(17) (see FIG. 5(b)).

The inner-threaded cylinder(17) and the outer-threaded rod(16) which are formed between the front and rear supporting members, are in mesh with each other. Also the objective lens cases(14L, 14R) are inserted into the eyepiece cases(11L, 11R). Therefore, when actuacting the adjusting knob(4), the eyepiece and objective lens cases(14L, 14R; 11L, 11R) can be either withdrawn or extended so as to achieve an optimal focus. In addition, the eyepiece cases(11L, 11R) can be folded about the axis of the cylinder(17), the rod(16) and the adjusting knob(4) (see FIG. 5(b)). Thus, the distance between the left and right lenses of the binoculars can be adjusted according to the user's eye distance by folding the above said apparatuses. As seen from the above, construction of a cap with light-weight binoculars according to the invention can be easily accomplished.

Figure 3A:
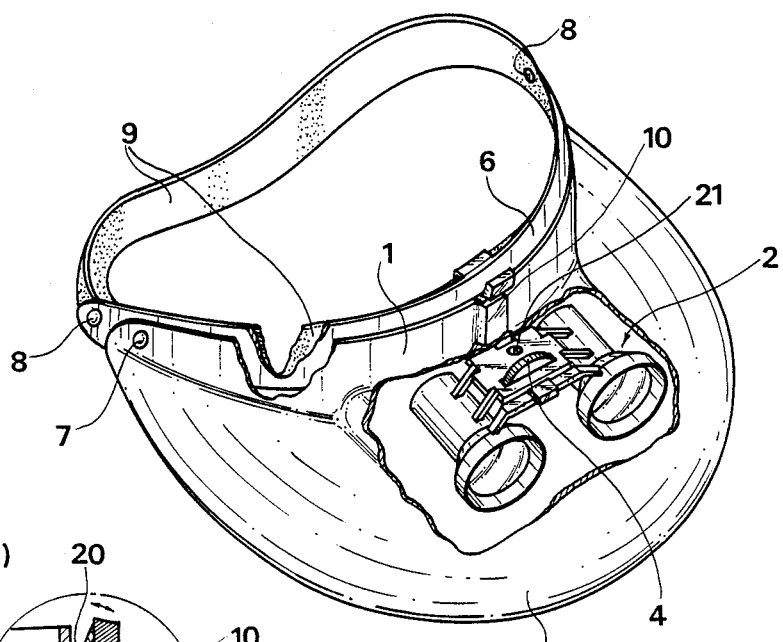
FIG. 3(a) is a perspective view showing the internal construction of the embodiment.

Binoculars, as illustrated above, are mounted on the cap so that the upper portion of the inner-threaded cylinder(17) is mounted to the binoculars receiving portion(2) by means of holding means(19) as illustrated in FIG.3(a).

Figure 3B:
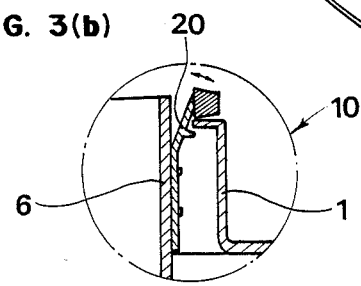
FIG. 3(b) is an enlarged sectional view of the latch forming portion and the supporting protrusion.
Figure 4A:
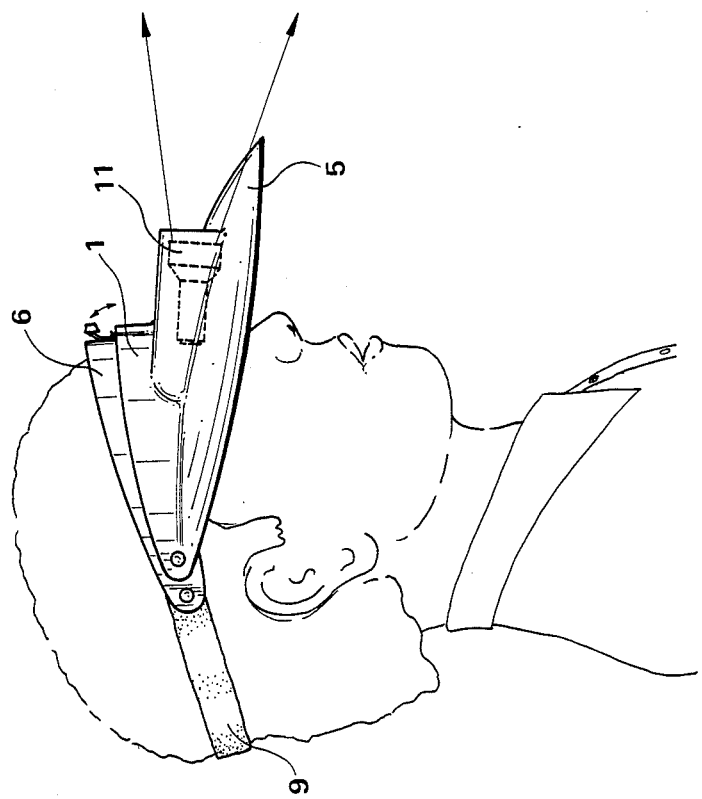
FIG. 4(a) and 4(b) illustrate usage of the embodiment.
Figure 4B:
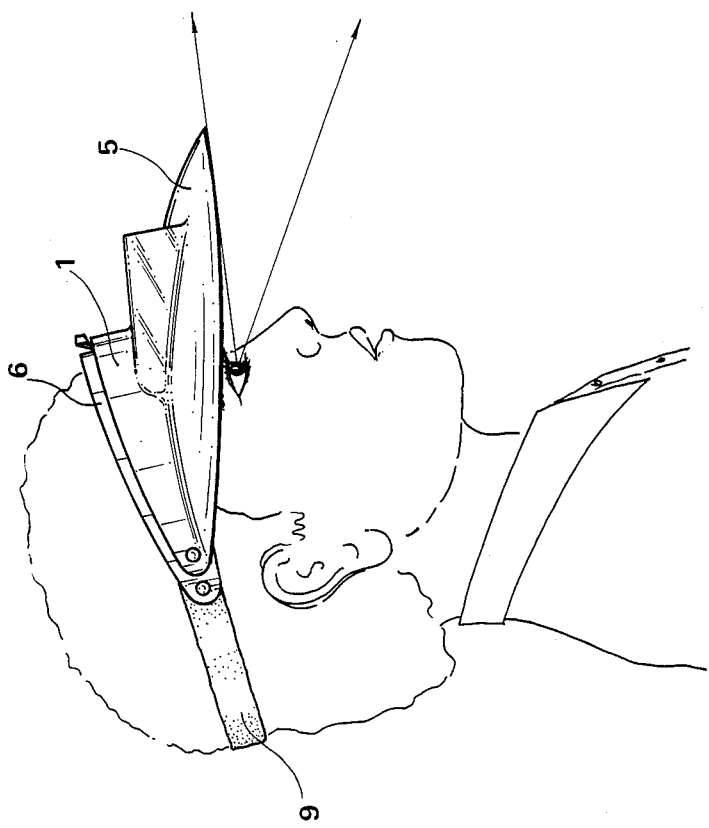

FIG. 4(a) shows when this invention is used as an ordinary cap. When a user wants to use the binoculars along with the cap, as illustrated FIG. 4(b), the user simply needs to pull down the visor(5) and fold the left and right eyepiece cases to adjust them to the distance desired, and focus the lenses with the adjusting knob(4). Similary, to return to a cap only, the user simply pushes the visor(5) up ward. Then, the latch(20) within the latch receiving groove(10) is caught on the supporting protrusion(21) as illustrated in FIG. 3(b).

This invention relates to a double functioning cap with the light-weight binoculars. When the total weight thereof is further reduced, not only will it be more idealistic to use both as a cap and binoculars, but also continuous uses of such binoculars for long hours are possible as well.

While there has been described what is at present considered to be preferred embodiment of the invention, it will be understood that various modifications may be made therein, and it is intended to cover in the appended claim all such modifications as fall within the true spirit and scope of the invention.

What is claimed is:

1. A cap with binoculars comprising:
    a head band adapted to be worn on the head of a user;
    a visor portion connected to said head band, said visor portion including a visor member and a binoculars receiving portion mounted on said visor member, said binoculars receiving portion having an upper surface with an opening therein;
    binoculars mounted within said binoculars receiving portion and adjustable therein according to distance for the eyes of the user wearing said head band, said binoculars having an adjusting knob adjustable by the user through said opening;
    a pin connecting means for connecting said visor portion to said head band such that said visor portion is movable between first and second positions relative to said head band when worn by the user, said visor portion when in the first position being positioned so that the user can see underneath said visor member, said visor portion when in the second position being positioned so that the user can look through said binoculars mounted in said binoculars receiving portion; and
    a latching means for releasably latching said visor portion relative to said head band in the first position when raised thereto.

2. The cap with binoculars of claim 1 wherein said binoculars receiving portion is integrally formed on said visor member.

3. The cap with binoculars of claim 1 wherein said visor portion includes a vertical visor semicircular portion attached to said visor member.

4. The cap with binoculars of claim 3 wherein said latching means includes a latch receiving groove formed in the center of said vertical visor semicircular portion.

5. The cap with binoculars of claim 4 wherein said head band includes a vertical head band semicircular portion, and said latching means includes a latch member connected to said vertical head band semicircular portion and engageable with said latch receiving groove.

6. The cap with binoculars of claim 1 wherein said head band includes a vertical head band semicircular portion having an outer surface, and said latching means includes a supporting protrusion formed on said outer surface.

7. The cap with binoculars of claim 1 wherein said binoculars receiving portion has protective glass at a forward location thereof for protecting said binoculars when mounted in said binoculars receiving portion.

8. The cap with binoculars of claim 1 wherein said visor member, when said visor portion is in the first position, is positioned to shade the user's eyes from the sun.

9. The cap with binoculars of claim 1 further comprising a holding means for holding said binoculars in said binoculars receiving portion when mounted therein.

10. The cap with binoculars of claim 1 wherein said visor portion includes a vertical visor semicircular portion connected to said visor member and having left and right pin holes therethrough, and said pin means includes left and right pins disposed in said left and right pin holes, respectively.

11. The cap with binoculars of claim 10 wherein said head band includes a resilient head band member and a vertical head band semicircular portion attached to said resilient head band member, and said left and right pins are connected to said vertical head band semicircular portion.

12. The cap with binoculars of claim 1 wherein said head band includes a resilient head band member, a vertical head band semicircular portion, and a hook means for connecting said resilient head band to said vertical head band semicircular portion.

13. The cap with binoculars of claim 1 wherein said latching means latches said visor portion at a forward location thereof above said visor member to said head band.

* * * * *